(12) United States Patent
Dupelle et al.

(10) Patent No.: US 9,737,701 B2
(45) Date of Patent: Aug. 22, 2017

(54) LONG TERM WEAR MULTIFUNCTION BIOMEDICAL ELECTRODE

(71) Applicant: ZOLL MEDICAL CORPORATION, Chelmsford, MA (US)

(72) Inventors: Michael R. Dupelle, North Attleboro, MA (US); Christopher Desmarais, Acuschnet, MA (US); Mark Totman, Winchester, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 13/907,268

(22) Filed: May 31, 2013

(65) Prior Publication Data
US 2013/0325096 A1 Dec. 5, 2013

Related U.S. Application Data

(60) Provisional application No. 61/653,749, filed on May 31, 2012.

(51) Int. Cl.
*A61N 1/18* (2006.01)
*A61N 1/04* (2006.01)
*A61B 5/0408* (2006.01)

(52) U.S. Cl.
CPC ........ *A61N 1/0496* (2013.01); *A61B 5/04087* (2013.01); *A61N 1/046* (2013.01); *A61N 1/0476* (2013.01)

(58) Field of Classification Search
CPC . A61B 5/04087; A61B 5/6833; A61B 5/6832; A61B 2562/14; A61N 1/0492;
(Continued)

(56) References Cited

U.S. PATENT DOCUMENTS 5,243,978 A 9/1993 Duffin, Jr.
6,148,233 A * 11/2000 Owen .................. A61N 1/0452
607/5

(Continued)

FOREIGN PATENT DOCUMENTS

JP S57-153634 A 9/1982
JP 2002521140 A 7/2002
(Continued)

OTHER PUBLICATIONS

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

(Continued)

*Primary Examiner* — Michael Kahelin
*Assistant Examiner* — Minh Duc Pham
(74) *Attorney, Agent, or Firm* — Lando & Anastasi, LLP

(57) ABSTRACT

Electrodes, multi-electrode patches, and electrodes for biomedical systems are provided. The electrode includes an adhesive film layer having a top surface and a bottom surface. A conductive element is substantially surrounded by the adhesive film layer. A conductive gel layer covers at least portion of a surface of the conductive element. The conducting gel comprises a material that does not result in significant skin irritation on a human subject after a period of at least about one week.

27 Claims, 7 Drawing Sheets

(58) Field of Classification Search
CPC . A61N 1/0484; A61N 1/0496; A61N 1/36125
USPC .................................. 607/116, 142; 600/391
See application file for complete search history.

(56) References Cited

U.S. PATENT DOCUMENTS

| | | | | |
|---|---|---|---|---|
| 6,792,301 | B2* | 9/2004 | Munro | A61B 5/04087 |
| | | | | 204/414 |
| 2007/0150039 | A1* | 6/2007 | Leigh | A61N 1/0541 |
| | | | | 607/152 |
| 2007/0196320 | A1 | 8/2007 | Yasin | |
| 2010/0228113 | A1* | 9/2010 | Solosko | A61B 5/0416 |
| | | | | 600/382 |
| 2013/0060115 | A1* | 3/2013 | Gehman | A61B 5/0416 |
| | | | | 600/372 |

FOREIGN PATENT DOCUMENTS

| | | |
|---|---|---|
| JP | 2006000658 A | 1/2006 |
| WO | 2007083275 A1 | 7/2007 |
| WO | 2009064641 A1 | 5/2009 |

OTHER PUBLICATIONS

Notification of Transmittal of the International Search Report and the Written Opinion of the International Searching Authority from corresponding PCT/US2013/043565 mailed Oct. 29, 2013.
"Biological Evaluation of Medical Devices—Part 10: Tests for Irritation and Skin Sensitization." American National Standard. ANSI/AAMI/IDSO 109993-10:2010.
Supplementary Partial European Search Report from corresponding EP Application No. 13796845.9 dated May 12, 2016.

* cited by examiner

A - A

| | Total | Apex | Sternum | Radius* | Diameter* | Length* | Width* | Pad Circumference |
|---|---|---|---|---|---|---|---|---|
| DF 80 compliant double round electrode system | 150.00 | 75.00 | 75.00 | 4.89 | 9.77 | | | 30.69 |
| DF 80 compliant double square electrode system | 150.00 | 75.00 | 75.00 | | | 8.66 | 8.66 | 34.64 |
| 4 segments (round) & 1/2 area | 75.00 | 37.50 | 37.50 | 1.73 | 3.46 | | | 43.41 |
| 4 segments (round) with equal circumference to double square | 47.77 | 23.89 | 23.89 | 1.38 | 2.76 | | | 34.64 |
| 4 segments (round) with equal circumference to double round | 37.50 | 18.75 | 18.75 | 1.22 | 2.44 | | | 30.69 |

\* For each electrode element

FIG. 7

LONG TERM WEAR MULTIFUNCTION BIOMEDICAL ELECTRODE

RELATED APPLICATIONS

This application claims priority under 35 U.S.C. §119(e) to U.S. Provisional Application Ser. No. 61/653,749, titled "LONG TERM WEAR MULTIFUNCTION BIOMEDICAL ELECTRODE," filed on May 31, 2012, which is herein incorporated by reference in its entirety.

BACKGROUND OF INVENTION

Embodiments of the present invention relate generally to biomedical electrodes, and more specifically, to transcutaneous electrodes configured to monitor and/or apply therapy to a subject.

SUMMARY OF INVENTION

Aspects and embodiments of the present invention are directed to a multifunction biomedical electrode, and to systems and methods of its use and manufacture. At least one electrode can be adhered to a subject to apply treatment in the form of an electric shock, for example, to defibrillate or pace the subject or to perform cardioversion. The electrode can also pass electrical energy to the subject to stimulate a portion of the subject's body, and/or can monitor the condition of the subject. The multifunction electrode may be fabricated from materials which facilitate long term use without causing significant irritation to the skin of a subject.

In accordance with an aspect of the present invention, there is provided an electrode. The electrode comprises an adhesive film layer having a first surface and a second surface opposite the first surface, a conductive element substantially surrounded by the adhesive film layer, and a conductive gel layer covering at least a portion of a surface of the conductive element. The combined impedance of the conductive element and the conductive gel layer is less than about 3 Ohms at maximum energy and the conductive gel forming the conductive gel layer may comprise a material that does not result in significant skin irritation on a human subject as tested in accordance with the method of ANSI/AAMI/ISO standard 10993-1 after a period of at least about one week. In accordance with an embodiment of the present invention, the electrode may be included in an electrode system wherein the electrode system and subject (to whom the electrode system is applied) may typically have a combined impedance of less than about 200 Ohms when measured during a defibrillation event or during the application of a low energy pulse used to measure the subject's impedance. It should be appreciated that the combined impedance of the electrode system and the subject may vary dependent upon the impedance of the subject, the size and type of electrode (e.g., a segmented or non-segmented electrode), the type of conductive gel used, etc. The distribution of impedances for such a combined electrode system and subject may vary from about 20 Ohms to about 200 Ohms, or more typically from about 50 Ohms to about 175 Ohms, and more typically from about 85 Ohms to about 115 Ohms when measured across a population of subjects using various electrodes compliant with the ANSI/AAMI DF80:2003 medical electrical equipment standard for the safety of cardiac defibrillators (DF compliant electrodes) with conductive gel areas of 150 cm².

In accordance with some embodiments, the electrode is compliant with the ANSI/AAMI DF80:2003 medical electrical equipment standard for the safety of cardiac defibrillators. In accordance with other embodiments, the electrode provides similar performance as electrodes compliant with the ANSI/AAMI DF80:2003 medical electrical equipment standard for the safety of cardiac defibrillators.

In accordance with some embodiments, the conductive gel is a hydrogel comprising an aqueous plasticizer, a copolymer of a hydrophilic unsaturated water-soluble first monomer, a hydrophilic unsaturated water-soluble second monomer, and a cross-linking agent.

In accordance with some embodiments, the first monomer is a compound of the formula

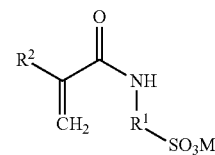

wherein $R^1$ is selected from the group consisting of a hydrocarbon moiety, a hydroxyl group, an amino group, an ammonium group, a halogen, and an alkali metal cation, $R^2$ is selected from the group consisting of hydrogen, a methyl group, an ethyl group, a hydroxyl group, an amino group, an ammonium group, a halogen, and an alkali metal cation, and M is selected from the group consisting of hydrogen and a cation.

In accordance with some embodiments, $R^1$ is selected from the group consisting of alkyl, cycloalkyl, and an aromatic moiety containing from 3 to 12 carbon atoms.

In accordance with some embodiments, $R^1$ represents

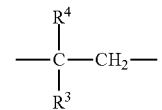

wherein $R^3$ is selected from the group consisting of hydrogen, an alkyl group possessing from 1 to 6 carbon atoms, a hydroxyl group, an amino group, an ammonium group, a halogen, and an alkali metal cation, and $R^4$ selected from the group consisting of an alkyl group possessing from 1 to 6 carbon atoms, a hydroxyl group, an amino group, an ammonium group, a halogen, and an alkali metal cation.

In accordance with some embodiments, the second monomer is a compound of the formula

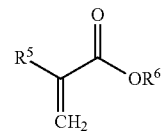

wherein $R^5$ is selected from the group consisting of hydrogen, a methyl group, an ethyl group, a hydroxyl group, an amino group, an ammonium group, a halogen, and an alkali metal cation, $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

In accordance with another aspect of the present invention, there is provided an electrode patch. The electrode patch comprises an adhesive film layer having a first surface and a second surface opposite the first surface and a plurality of electrodes. At least one of the plurality of electrodes includes a conductive element substantially surrounded by the adhesive film layer and a conductive gel layer covering at least a portion of a surface of the conductive element. The combined impedance of the conductive element and the conductive gel layer is less than about 3 Ohms at maximum energy and the conductive gel forming the conductive gel layer comprises a material that does not result in significant skin irritation on a human subject as tested in accordance with the method of ANSI/AAMI/ISO standard 10993-1 after a period of at least about one week.

In accordance with some embodiments, the electrode patch provides similar performance as electrodes compliant with the ANSI/AAMI DF80:2003 medical electrical equipment standard for the safety of cardiac defibrillators.

In accordance with some embodiments, the conductive gel layer of at least one of the plurality of electrodes is a hydrogel comprising an aqueous plasticizer, a copolymer of a hydrophilic unsaturated water-soluble first monomer, a hydrophilic unsaturated water-soluble second monomer, and a cross-linking agent.

In accordance with some embodiments, the first monomer is a compound of the formula

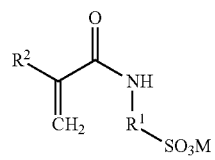

wherein $R^1$ is selected from the group consisting of a hydrocarbon moiety, a hydroxyl group, an amino group, an ammonium group, a halogen, and an alkali metal cation, $R^2$ is selected from the group consisting of hydrogen, a methyl group, an ethyl group, a hydroxyl group, an amino group, an ammonium group, a halogen, and an alkali metal cation, and M is selected from the group consisting of hydrogen and a cation.

In accordance with some embodiments, the second monomer is a compound of the formula

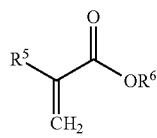

wherein $R^5$ is selected from the group consisting of hydrogen, a methyl group, an ethyl group, a hydroxyl group, an amino group, an ammonium group, a halogen, and an alkali metal cation, $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

In accordance with some embodiments of the electrode patch, a first of the plurality of electrodes and a second of the plurality of electrodes are spaced equidistant from a third of the plurality of electrodes.

In accordance with some embodiments of the electrode patch, at least two of the plurality of electrodes share a common electrical connection.

In accordance with some embodiments of the electrode patch, at least two of the plurality of electrodes can be selectively electrically coupled together.

In accordance with another aspect of the present invention, there is provided a biomedical electrode system. The biomedical electrode system comprises a first electrode configured to adhere to a first location of a subject and a second electrode configured to adhere to a second location of the subject. The first electrode includes an adhesive film layer having a first surface and a second surface opposite the first surface, a conductive element substantially surrounded by the adhesive film layer, and a conductive gel layer covering at least a portion of a surface of the conductive element. The combined impedance of the conductive element and the conductive gel layer is less than about 3 Ohms at maximum energy and the conductive gel forming the conductive gel layer comprises a material that does not result in significant skin irritation on a human subject as tested in accordance with the method of ANSI/AAMI/ISO standard 10993-1 after a period of at least about one week.

In accordance with some embodiments, the conductive gel layer comprises a material that does not result in significant skin irritation on a human subject as tested in accordance with the method of ANSI/AAMI/ISO standard 10993-1 after a period of at least about two weeks.

In accordance with some embodiments, the conductive gel layer of at least one of the plurality of electrodes is a hydrogel comprising an aqueous plasticizer, a copolymer of a hydrophilic unsaturated water-soluble first monomer, a hydrophilic unsaturated water-soluble second monomer, and a cross-linking agent.

In accordance with some embodiments, the first monomer is a compound of the formula

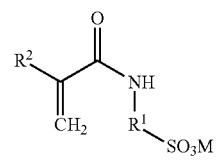

wherein $R^1$ is selected from the group consisting of a hydrocarbon moiety, a hydroxyl group, an amino group, an ammonium group, a halogen, and an alkali metal cation, $R^2$ is selected from the group consisting of hydrogen, a methyl group, an ethyl group, a hydroxyl group, an amino group, an ammonium group, a halogen, and an alkali metal cation, and M is selected from the group consisting of hydrogen and a cation.

In accordance with some embodiments, the second monomer is a compound of the formula

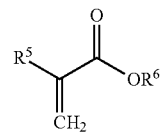

wherein $R^5$ is selected from the group consisting of hydrogen, a methyl group, an ethyl group, a hydroxyl group, an amino group, an ammonium group, a halogen, and an alkali metal cation, $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

These and other aspects and embodiments are discussed in detail below. The foregoing information and the following detailed description include illustrative examples of various aspects and embodiments, and provide an overview or framework for understanding the nature and character of the claimed aspects and embodiments. The drawings provide illustration and a further understanding of the various aspects and embodiments, and are incorporated in and constitute a part of this specification. The drawings, together with the remainder of the specification, serve to describe and explain the claimed aspects and embodiments.

BRIEF DESCRIPTION OF DRAWINGS

The accompanying drawings are not intended to be drawn to scale. In the drawings, each identical or nearly identical component that is illustrated in various FIGS. is represented by a like numeral. For purposes of clarity, not every component may be labeled in every drawing. In the drawings:

FIG. 7 is a table illustrating the dimensions of various electrode system configurations.

DETAILED DESCRIPTION

Figure 1:
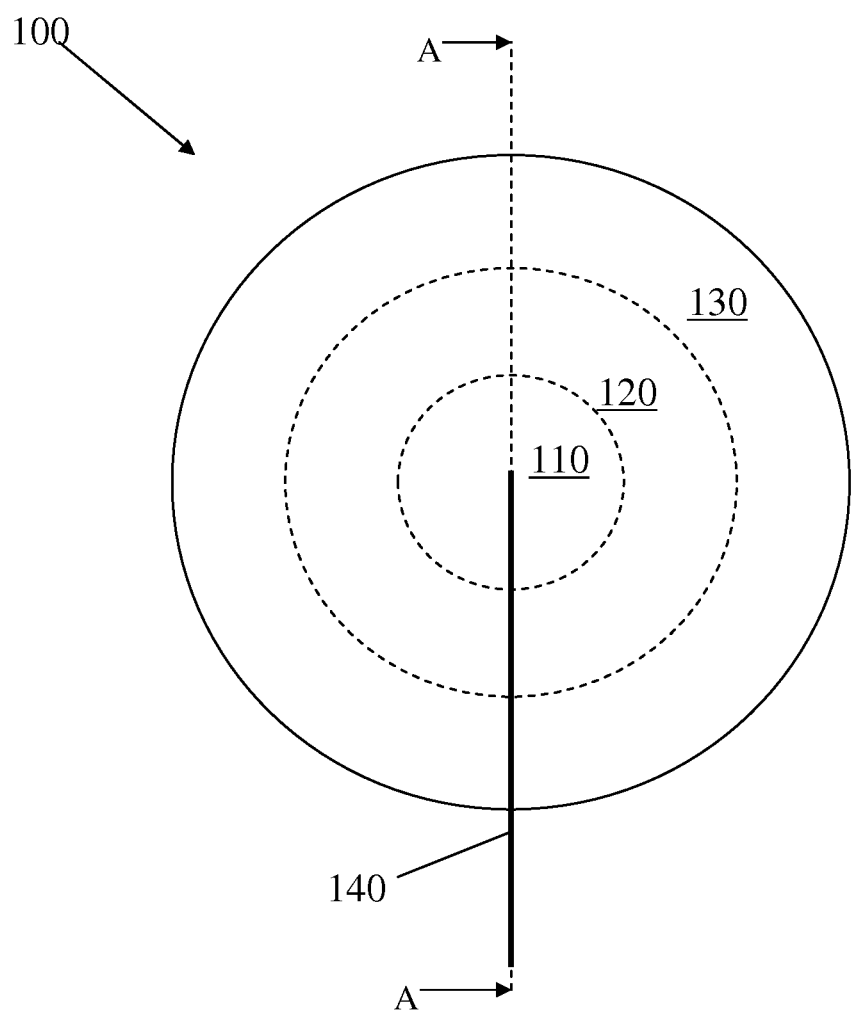
FIG. 1 is a plan view depicting an electrode in accordance with an embodiment of the present invention.

The systems and methods described herein are not limited in their application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter, equivalents thereof, and additional items, as well as alternate embodiments consisting of the items listed thereafter exclusively.

Biomedical electrodes (referred to herein as simply "electrodes") may be used for defibrillating, pacing, cardioversion, and/or monitoring the activity of a subject's heart. The electrodes disclosed herein are suitable for use on human subjects, although use on non-human subjects is also contemplated. Embodiments of electrodes as disclosed herein can be coupled with power sources and control logic to deliver electrical energy to a subject, to determine the timing, levels, and history of applied energy, and to process monitored or detected data for analysis by, for example, a health care provider. Embodiments of electrodes as disclosed herein can may be located proximate to the subject, for example, attached, connected, or coupled to the subject, at an anterior, posterior, lateral, or other location on the subject. For example, embodiments of electrodes as disclosed herein can be attached to the subject's chest, back, side, head, abdomen, torso, thorax, or legs. In some embodiments the electrodes disclosed are external electrodes configured to be attached to the subject proximate to the subject's heart. Embodiments of electrodes as disclosed herein can be disposable or can be configured for repeated use.

In various instances it may be desirable to pace and/or monitor the heart of a subject with non-invasive, externally placed electrodes for an extended period of time, for example, while the subject is recovering from a heart attack, surgery, or other injury to the heart, while awaiting a heart transplant, or to monitor and/or protect a subject at risk of syncope. In some prior art externally-attached biomedical electrodes, attachment of the electrodes to the skin of a subject may result in skin irritation at the point of attachment within a relatively short period of time ranging, for example, from about a few hours to about a few days. Extended-wear electrodes in accordance with embodiments of the present invention are constructed of materials, for example, adhesive films and conductive hydrogels, which reduce the occurrence of skin irritation and/or extend the time for which the electrode may be comfortably attached to the skin of a subject.

In some embodiments, extended-wear electrodes in accordance with the present invention may be worn continuously by a subject for a time period in excess of, for example, three days, for a week or more, or for up to about two weeks or more without the subject experiencing significant skin irritation due to the attachment of the electrode to the skin of the subject. As used herein "significant skin irritation" is defined as corresponding to a skin irritation grading of one (a weakly positive reaction usually characterized by mild erythema and/or dryness across most of the treatment site) or more as set forth in Table C.1 of Annex C of AANI/AAMI/ISO standard 210993-10:2010 when electrodes are tested on human subjects in accordance with the method set forth in this standard. As used herein, the terms "long-term wear" or "extended-wear" refer to continuous or substantially continuous contact of an electrode with the skin of a subject for a time period in excess of, for example, a week or more. Some embodiments of extended-wear electrodes disclosed herein may have the ability to apply a defibrillation charge to, or perform cardioversion on, a subject wearing the electrodes in addition to monitoring and/or pacing the heart of a subject. Embodiments of the electrodes disclosed herein may be compliant with the ANSI/AAMI DF80:2003 medical electrical equipment standard for the safety of cardiac defibrillators.

In some embodiments, extended-wear electrodes in accordance with the present invention may facilitate the reduction in skin irritation when used for "long-term wear" or "extended-wear" regimens by providing for the passage of water vapor, for example, from a subject's sweat through the electrode. Extended-wear electrodes in accordance with the present invention may exhibit a moisture vapor transmission rate (MVTR) of, for example between about 600 $g/m^2/day$ and about 1,400 $g/m^2/day$ when worn by a subject in an environment at room temperature and at a relative humidity of, for example, about 70%.

Extended-wear electrodes in accordance with embodiments of the present invention may provide numerous advantages over prior art electrodes. Providing for extended-wear of the electrodes may reduce the number of electrodes consumed over a given period of time, reducing the cost associated with replacing electrodes which are not suitable for use in extended-wear scenarios, for example, for time periods greater than about a week. Discomfort of a subject associated with wearing the electrodes may be decreased due to a reduction in skin irritation caused by the extended-wear electrodes as compared to conventional electrodes. Discomfort of a subject associated with wearing the electrodes may also be decreased due to a reduction in the number of times which an extended-wear electrode may need to be removed from the skin of the subject or repositioned, resulting in possible damage to the underlying skin, as compared to conventional electrodes. Further, accuracy of monitoring of the heart of a subject may be facilitated by the use of extended-wear electrodes by keeping the monitoring electrodes in the same position rather than replacing them and mounting them in potentially different positions as may occur with electrodes which should be replaced frequently or repositioned due to the occurrence of skin irritation.

Electrodes in accordance with some embodiments of the present invention may be combined in multi-electrode patches or as part of a long-term wear device, for example, as part of known non-invasive bodily-attached ambulatory medical monitoring and treatment devices, such as the LifeVest® Wearable Cardioverter Defibrillator available from ZOLL Medical Corporation. Electrodes in accordance with some embodiments of the present invention may be used in syncope monitoring and/or treatment devices such as described in the U.S. application Ser. No. 13/907,406 and titled SYSTEMS AND METHODS FOR DETECTING HEALTH DISORDERS.

When combined in a multi-electrode patch, individual electrodes may perform different functions, for example, one or more of pacing, monitoring, defibrillating, and cardioversion and may have characteristics, for example, surface area or conductivity, which are tailored for the particular function(s) the individual electrodes are intended to perform.

Figure 2:
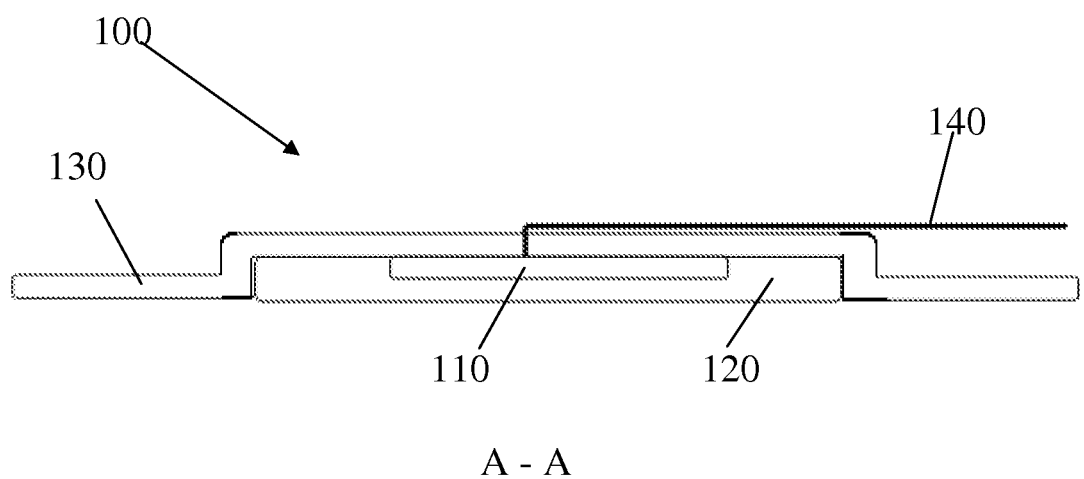
FIG. 2 is a cross section of the electrode of FIG. 1 through line A-A.

A generalized illustration of embodiment of an electrode in accordance with the present invention, indicated generally at 100, is shown in plan view in FIG. 1, and in cross section in FIG. 2. The electrode 100 includes a conductive element 110, which may comprise a metal, for example, tin or aluminum, a conductive ink, a conductive polymer, or any other conductive material known in the art. The conductive element 110 may be in the form of a thin film. The conductive element is substantially surrounded by a conductive gel layer 120. In some embodiments, the conductive gel layer 120 has a greater surface area than the conductive element 110, and in other embodiments, the surface areas of the conductive element 110 and the conductive gel layer 120 may be substantially similar, or the conductive element 110 may have a greater surface area than the conductive gel layer 120. Preferably the conductive gel layer 120 covers the surface of the conductive element 110. The conductive element 110 and conductive gel layer 120 are substantially surrounded by an adhesive film layer 130. The adhesive film layer 130 includes an adhesive on at least a portion of a surface thereof and may be used to adhere the electrode to the skin of a subject and to maintain the conductive gel layer 120 in electrical contact with the skin of the subject. The adhesive film layer 130 confines the conductive gel layer 120 and prevents conductive gel from escaping from an area covering the surface of the conductive element 110.

The adhesive film layer 130 is in some embodiments substantially non-conductive such that electrical current cannot pass from the conductive element 110 or conductive gel layer 120 through the adhesive film layer 130. In some embodiments, the conductive gel layer 120 may be sufficiently adhesive to skin that the adhesive film layer 130 may be omitted. The conductive element 110 is electrically connected to an electrical conductor 140 which may comprise, for example, a metal wire. The electrical conductor 140 may in use communicate with an external circuit which may utilize the electrode for monitoring, pacing, and/or defibrillating a subject's heart. In other embodiments, the electrode may include or be coupled to circuitry which communicates wirelessly with an external control and/or monitoring circuit. Although not depicted in FIGS. 1 and 2, the electrical conductor 140 may be physically and electrically connected to a connector, which may then be connected to and disconnected from external circuitry by a mating connector, each of which may be waterproof. Alternatively, the electrical conductor 140 may be formed from a material, such as gold, which can withstand exposure to the elements and repeated connections to and disconnections from the external circuitry.

As shown most clearly in FIG. 2, in one embodiment, the electrical conductor 140 extends through a central region of the adhesive film layer 130, such that the entire perimeter of the adhesive film layer 130 is in intimate contact with the subject's skin, unobstructed by the presence of the electrical conductor 140. A strain relief (not shown) may be used to hold the electrical conductor 140 in a fixed position with respect to the adhesive film layer 130.

Figure 3:
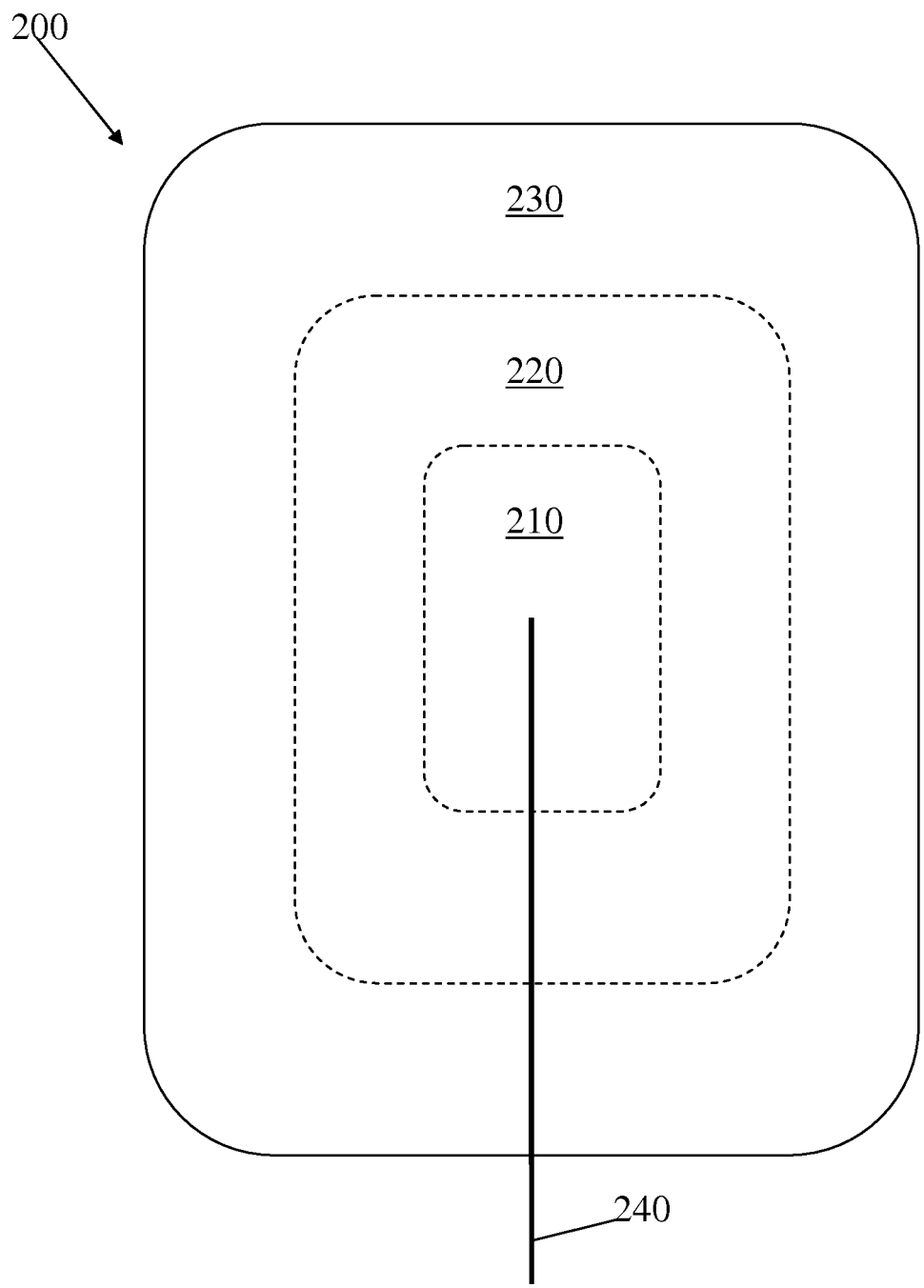
FIG. 3 is a plan view depicting an electrode in accordance with another embodiment of the present invention.

The electrode 100 is illustrated in FIG. 1 as substantially circular, however, other shapes are also contemplated. For example, as illustrated in FIG. 3, an electrode 200 may have a substantially rectangular shape with a substantially rectangular conductive element 210 connected to an electrical conductor 240, a substantially rectangular conductive gel layer 220, and a substantially rectangular adhesive film layer 230. The present invention is not limited to any particular shape of an electrode or of the components thereof and any one or more components of an electrode in accordance with the present invention may have different shapes than those illustrated. For example, an electrode or one or more of the components thereof may be oval, triangular, square, pentagonal, or any other shape desired. The overall shape of the conductive element 210 may differ from that of the conductive gel layer 220 and/or the adhesive film layer 230.

Electrodes in accordance with the present invention may include additional features not illustrated, for example, adhesive layers bonding the various components of the electrode together, labeling, a mechanism for holding the electrical conductor in place and in electrical contact with the conductive element, and/or packaging. Exemplary additional features are disclosed in co-pending U.S. patent application Ser. No. 13/079,336, titled BIOMEDICAL ELECTRODE, which is hereby incorporated herein by reference in its entirety. Components of electrodes in accordance with embodiments of the present invention may be formed from materials having certain desirable properties. For example, an electrode may be formed of materials that render it radiolucent or radiotransparent, as disclosed in co-pending U.S. patent application Ser. No. 13/079,336. Further, although not depicted in FIGS. 1-3, electrodes in accordance with the present invention may communicate wirelessly with other circuitry.

Electrodes in accordance with the present invention may be substantially flat. For example, electrodes 100, 200 may have a flat profile that is not noticeable or is minimally noticeable when attached to the subject, under the subject's clothes. Electrodes 100, 200 may also be substantially flexible. For example, electrodes 100, 200 can conform to the contours of the subject's body during initial attachment to the subject, and can conform to body positioning changes when the subject is in motion. Electrodes 100, 200 can also be substantially devoid of rigid components, such as hard snaps, connectors, and rigid plates. For example, electrodes 100, 200 may be devoid of hard rigid substances that may cause uncomfortable pressure points when a subject with electrodes 100, 200 attached to his/her body is in a prone, prostrate, supine, or lateral position with electrodes 100, 200 pressed against an object, such as a bed, couch, medical examining table, clothes, or medical equipment.

In some embodiments, at least a portion of the adhesive film layer which is arranged to contact the subject comprises a material that facilitates long-term wear of the electrode without causing significant skin irritation in the area of contact with the subject. Preferably, the adhesive film layer is formed from a flexible, waterproof, yet breathable material that permits the passage of water vapor away from the subject. Suitable materials may include, for example, polyurethane or Tegaderm™ wound care dressings, available from 3M, or other non-woven polymers. The use of such materials permits the electrode to be attached to the skin of the subject in a manner familiar to most medical professionals, such as a medical technician, emergency room nurse, or doctor. In one embodiment, the adhesive film layer has a thickness of about 0.16 cm ($\frac{1}{16}^{th}$ of an inch). In other embodiments, the adhesive film layer can have other thicknesses, for example, less than 0.16 cm or more than 0.16 cm. For example, Tegaderm™ wound care dressings are commonly available in a variety of thicknesses, such as consumer grade (less than 0.013 cm (5 mil) thick) and hospital grade (0.013-0.018 cm (5-7 mil) thick).

The surface area of the conductive gel layer which contacts the skin of the subject may be varied in accordance with various factors such as, for example, the surface area of the conductive element of the electrode, the magnitude of the current and/or voltage to be delivered to the subject, or the magnitude of the signal to be monitored. For example, the surface area of the conductive gel layer may be larger when the electrode is intended to deliver an electric charge for defibrillation or cardioversion to a subject than when the electrode is designed to monitor or pace a subject. A larger surface area, for a given conductivity of the conductive gel layer, would decrease the current density of electricity applied to the subject, thus reducing the potential for electrical burns and/or discomfort of the subject. In other embodiments, where the electrode is intended to deliver charge to a subject in a precise location, the conductive gel layer may be formed with a smaller surface area. The conductivity of the conductive gel may also be a factor is determining an appropriate surface area of the conductive gel. The surface area and the conductivity of the conductive gel layer are factors in determining the total impedance of the conductive gel layer. In some embodiments, the surface area of the conductive gel layer may be from about 64.5 $cm^2$ (10 $in^2$) to about 150 $cm^2$ (23.25 $in^2$) total (e.g., 75 $cm^2$ per electrode) for the electrodes in an electrode system, although this area may vary depending upon the purpose of the electrode(s) and the conductivity of the conductive gel layer. In electrode systems including multi-electrode patches, each individual electrode segment may be circular, and have a radius from about 1.22 cm (4.7 $cm^2$ in area) to about 1.73 cm (9.4 $cm^2$ in area). Electrode systems including multi-electrode patches may have total electrode surface areas of as small as about 37.5 $cm^2$ (5.8 $in^2$) to about 75 $cm^2$ (11.6 $in^2$). As discussed in more detail below, a multi-electrode patch may include electrodes having a total surface area which is significantly smaller than the effective surface area of the electrodes. The effective surface area of the electrodes is the surface area of a single electrode patch which would perform equivalently for the delivery of electric charge to a subject as the multi-electrode patch.

Different functions of the electrode may be preferentially performed with electrodes having different impedances. As used herein, the impedance of an electrode is defined as the impedance between a conductive element of the electrode and the skin of the subject to which the electrode is attached, and including any gel layer disposed between the conductive element and the subject's skin. For example, when used for defibrillation, an electrode may desirably have a low impedance of less than about three Ohms. When used for defibrillation, the combined impedance of an electrode system including two electrodes, any conductive gel, and the subject (to whom the electrode system is attached) will typically be less than about 200 Ohms when measured during a defibrillation event or during the application of a low energy pulse used to measure the subject's impedance. It should be appreciated that the combined impedance of the electrode system and the subject may vary depending on the impedance of the subject, the size and type of electrode (e.g., a segmented or non-segmented electrode), the type of conductive gel used, etc. Generally, the distribution of impedances for such a combined electrode system and subject may vary from about 20 Ohms to about 200 Ohms, although ranges of between about 50 Ohms to about 175 Ohms, or between about 85 Ohms and about 115 Ohms may be more common.

When used for pacing, the impedance may desirably be higher to facilitate a reduction in a subject's discomfort, for example, between approximately 30 Ohms to approximately 100 Ohms or more. When used for pacing, the combined impedance of an electrode system including two electrodes, any conductive gel, and the subject will typically be between about 100 Ohms to about 300 Ohms, or more. When used for monitoring, the impedance may desirably be low, for example, three Ohms or less, so that weak electrical signals from a subject with a low signal-to-noise ratio can be accurately sensed. One or both of the conductive gel layer conductivity and surface area may be varied to obtain a desired impedance. The conductive gel layer of electrodes in accordance with the present invention may be formed of a material which gives the electrode an impedance that will satisfy the impedance requirements set forth in the ANSI/AAMI DF80:2003 medical electrical equipment standard for the safety of cardiac defibrillators.

Figure 4:
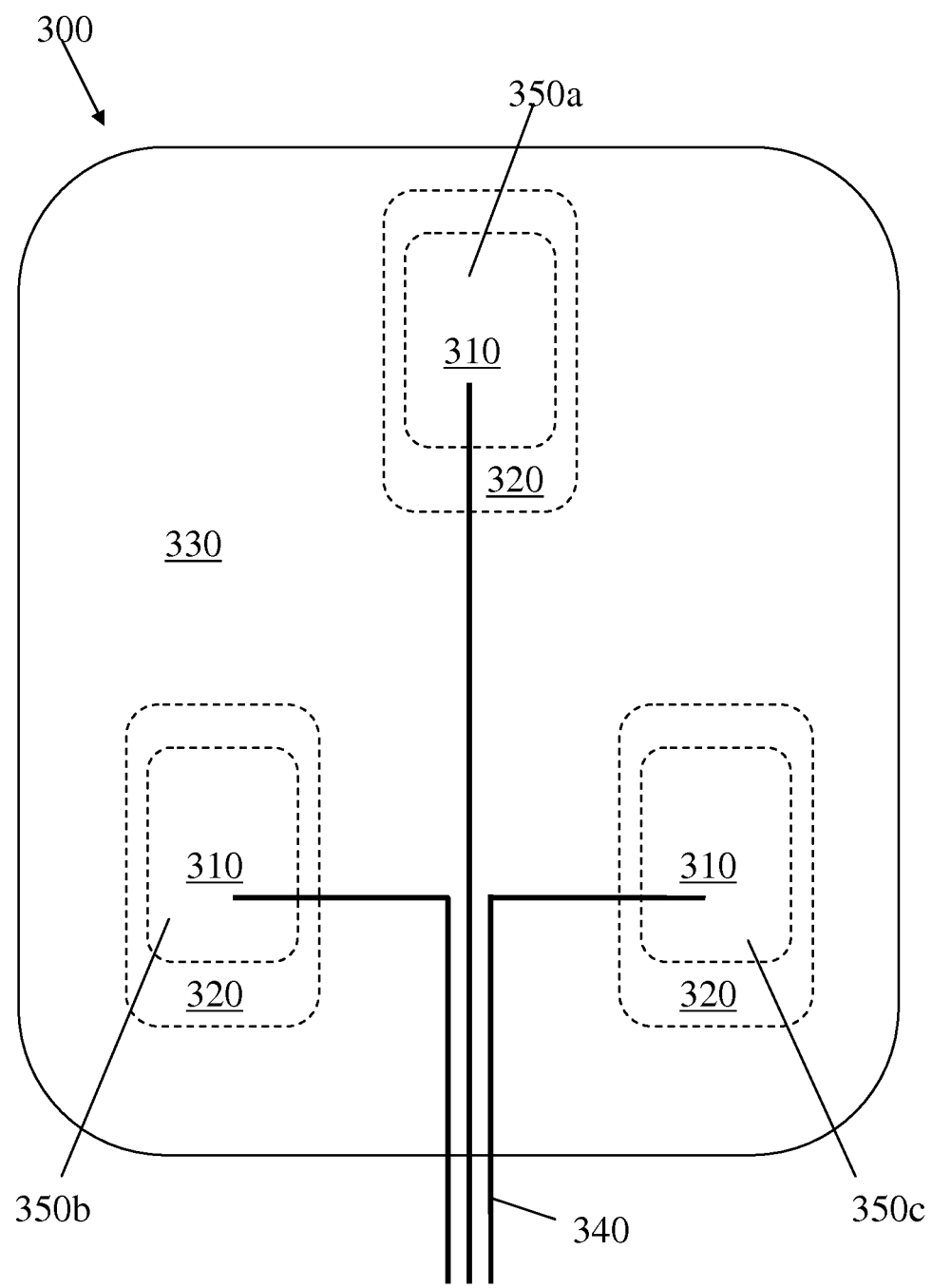
FIG. 4 is a plan view depicting a multi-electrode patch in accordance with another embodiment of the present invention.

Embodiments of the present invention may include two or more electrodes combined into a single electrode unit or patch and sharing a common adhesive film layer. An example of a patch including three electrodes 350a, 350b, and 350c is illustrated in FIG. 4, indicated generally at 300. The individual electrodes are mounted on a common adhesive film layer 330 in a generally triangular configuration. The adhesive film layer 330 may be constructed of similar materials as the adhesive film layer 130, 230 described above with reference to FIG. 1 and FIG. 3. Each electrode includes a conductive element 310 and a conductive gel layer 320, which may be similar to conductive element 110 or 210 and conductive gel layer 120 or 220, respectively, as described above with reference to the electrodes 100, 200 of FIG. 1 and FIG. 3. Each conductive element 310 is electrically connected to a respective electrical conductor 340, such as a wire. Each respective electrical conductor 340 may terminate in a common connector (not shown) to permit the electrode patch 300 to be electrically coupled to external circuitry. In the embodiment depicted in FIG. 4, each electrical conductor 340 extends through the adhesive film layer 330 in a central region of a respective electrode 350a, 350b, 350c, so that the entire perimeter of the adhesive film layer 330 is in intimate contact with the subject's skin, unobstructed by the presence of the electrical conductors 340. A strain relief (not shown) may again be used to hold the electrical conductors 340 in a fixed position with respect to the adhesive film layer 330.

In some embodiments, the conductive gel areas 320 of each electrode 350a, 350b, 350c may have dimensions of about 14.5 cm$^2$ (2.25 in$^2$). In some embodiments, the conductive gel areas 320 may be significantly smaller. In different electrodes, different conductive gel areas may be utilized. In general, the conductive gel areas will typically have an area that is slightly larger than the area of the corresponding conductive element 310. In some embodiments, the three electrodes are of different shapes, sizes, or types, and different electrodes in a single electrode unit or patch may be the same as each other, or at least one electrode may be shaped or sized differently or composed of different materials than at least one other electrode. The size, shape, and materials of the electrodes may be selected based on the function(s) the electrodes are intended to perform. In some embodiments, a subject would be fitted with two electrode patches 300 for purposes of cardiac pacing, monitoring, defibrillation and/or cardioversion.

In some embodiments at least two of the electrodes, for example, electrodes 350b and 350c may be spaced equidistant from a third of the electrodes, for example, electrode 350a, as described in U.S. Pat. No. 8,185,199, to Lisogurski et al., issued May 22, 2012, which is hereby incorporated herein by reference in its entirety. This may facilitate monitoring of the subject using electrodes 350b and 350c while a charge, for example, for pacing or defibrillation, is applied to the subject through electrode 350a. If the electrodes 350b and 350c are substantially equidistant from electrode 350a, any signal observed at electrodes 350b and 350c due to charge applied through electrode 350a would be substantially similar, and could be electronically compensated for by monitoring circuitry to which electrodes 350b and 350c are communicatively coupled to calculate a signal that would have been observed at electrodes 350b and 350c in the absence of the signal caused by electrode 350a.

By arranging the electrodes in a triangular pattern under the singular backing pad, only limited areas of skin are in contact with conductive gel. The triangular pattern allows the electrode unit to be removed and a new one re-applied in a different orientation, for example, inverted so that three new areas of skin are in contact with the conductive gel. This procedure may provide for an electrode unit to be applied to a substantially same area of the body of a subject for an extended period of time while reducing the potential for skin irritation due to long term occlusion of the surface of the skin by the electrodes.

In some embodiments, each of the individual electrodes 350a, 350b, and 350c can be electrically connected to one another, either in the electrode patch 300 or in a device to which the electrode patch is electrically connected. In other embodiments, one or more of the electrodes 350a, 350b, 350c can be connected to a distinct circuit from at least one other of the electrodes and used for a different purpose (for example, monitoring, pacing, defibrillation and/or cardioversion). In yet a further embodiment, selection circuitry may be provided to permit each electrode to be selectively electrically coupled to another, such that one or more of the electrodes 350a, 350b, and 350c could be utilized for a different purpose than at least one other of these electrodes during a concurrent time period. For example, in some embodiments, each electrode 350a, 350b, 350c in each of two electrode patches 300 can have a separate connection point and a separate wire connecting to a monitoring/defibrillation device and each set of three electrodes in a respective electrode patch 300 can be selectively combined for defibrillation and/or for pacing. The use of multiple electrodes during pacing can help to reduce the amount of discomfort of the subject relative to the use of a single electrode. For example, a pacing pulse of 15 msec (or longer) in duration may be applied to the subject by applying at least three 5 msec (or shorter) pacing pulses in sequence to each electrode 350a, 350b, 350c. At other times, for example, during monitoring, various ECG vectors could be established between the six electrodes acting as separate electrodes. In some embodiments, a pacing pulse might be sent through two electrodes in one electrode patch to "wake up" a non-responsive subject.

In some embodiments, the conductivity of the conductive gel layer 320 beneath the conductive element 310 of one of the electrodes (e.g., electrode 350a) may differ from the conductivity of the conductive gel layer beneath the conductive element of the other electrodes (e.g., 350b and 350c). For example, the conductivity of the conductive gel layer 320 of electrode 350a may be optimized for pacing the subject, while the conductivity of the conductive gel layer of electrodes 350b and 350c may be optimized for defibrillation. In some embodiments, the conductivity of the conductive gel layer 320 of each electrode may differ from that of the others, with each being optimized for the desired functionality of the respective electrode.

Figure 5:
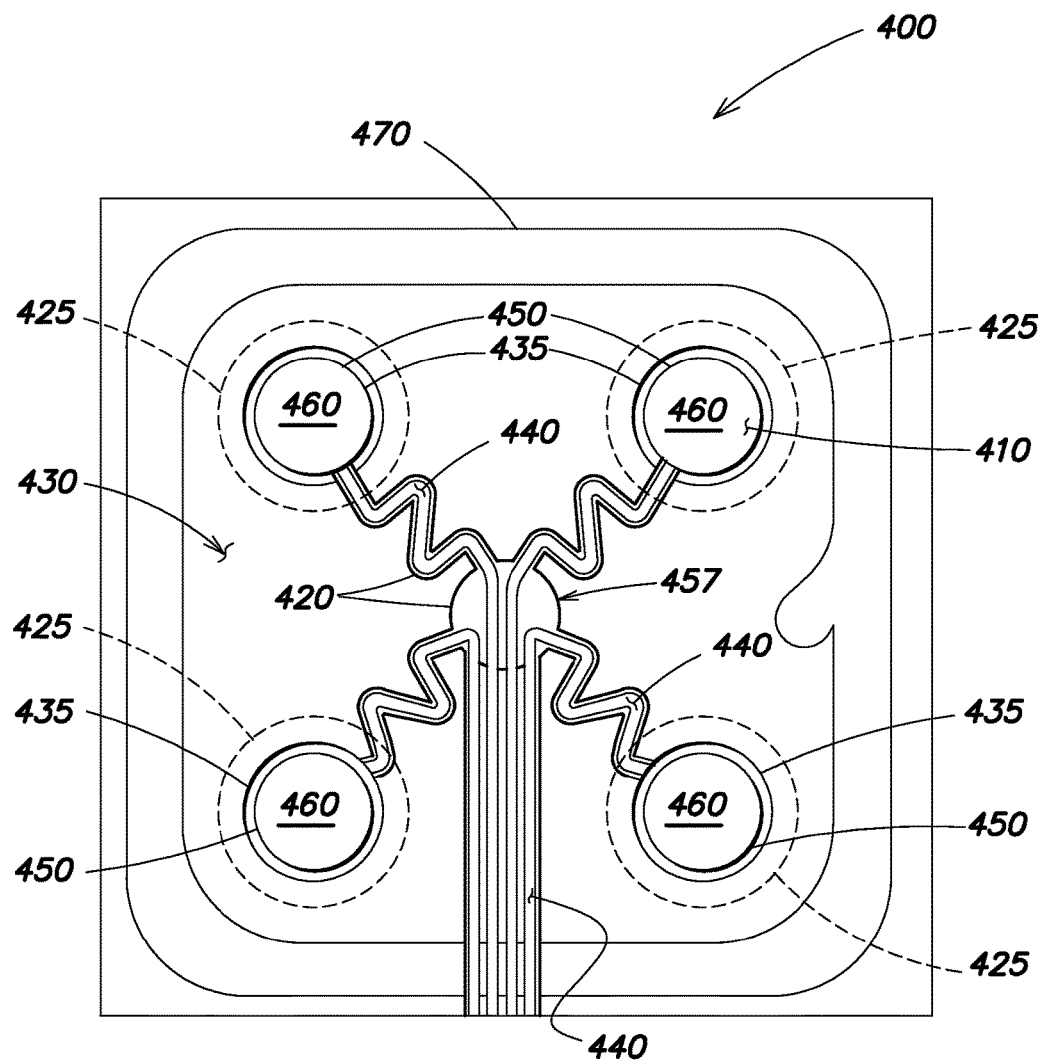
FIG. 5 is a plan view depicting a multi-electrode patch in accordance with another embodiment of the present invention.

In a further embodiment, an electrode patch 400, illustrated in FIG. 5, may include four electrodes 450. Each of the electrodes 450 may include a conductive element 410. The conductive element may be formed, for example, by sputtering or stencil printing a conductive material on a dielectric film, for example, a polyethylene terephthalate (PET) dielectric film 420. Each of the electrodes may include a conductive gel layer 425, which may be similar to conductive gel layers 120, 220 as described above with reference to the electrodes 100, 200 of FIG. 1 and FIG. 3. The electrodes may share a common adhesive film layer 430, which may be constructed of similar materials as the adhesive film layers 130, 230 described above with reference to FIG. 1 and FIG. 3. The electrodes 450 may be arranged substantially equidistant from one another. This may provide for a signal observed at a first two electrodes positioned equidistant from a third electrode which created the signal to be electronically subtracted from an overall signal observed at the first two electrodes, increasing the reliability of measurements from the first two electrodes. Each of the electrodes 450 may be electrically coupled to an electrical conductor 440, for example a metal wire, to provide for electrical coupling of the electrodes 450 (either by wires, or wirelessly) to external circuitry configured to monitor a subject and/or to apply pacing or defibrillation charges to the subject. Alternatively, the electrical conductors 440 may be formed by depositing a conductive material on the same dielectric film 420 used to form the conductive element 410, as illustrated in the embodiment depicted in FIG. 5. In one embodiment, the conductive material forming the electrical conductors may be coated with a insulating film to electrically isolate them from the adhesive film layer 430 and the subject's skin.

In some embodiments, one or more apertures 435 defined by openings in the adhesive film layer 430 may provide for the conductive elements 410 of the electrodes 450 to electrically and physically contact the conductive gel layers 425. This contact may occur at contact regions 460 of the conductive elements 410. As illustrated in FIG. 5, the conductive gel layer 425 for each electrode 450 is formed as a disk disposed on a side of the adhesive film layer opposite from the conductive elements 410. The apertures 435 may have one or more dimensions, for example, radii, that are smaller than one or more dimensions, for example, radii, of the conductive gel layers 425. Portions of the conductive gel layers 425 may thus extend below the adhesive film layer 430 beyond areas defined by the apertures 435. The contact regions 460 of the conductive elements 410, illustrated as disks centered in the apertures 435 in FIG. 5, may have one or more dimensions, for example, radii, that are smaller than one or more dimensions, for example, radii, of the apertures 435. This may provide for a spacing to be defined between portions or all of the contact regions 460 and inner edges of the apertures 435. This spacing may provide for the contact regions 460 and/or the entire electrodes 450 to move relative to the adhesive film layer 430 while maintaining contact with the conductive gel layers 425. This motion may help to prevent damage to the electrodes 450 due to movement of a subject to which the electrode patch 400 may be attached. The zig-zag shape of the portion of the conductive element 410 that connects to electrical conductors 440 may also permit the electrodes 450 to move with movement of the subject's skin, rather than shearing away. In some embodiments, the contact areas 460 and/or entire electrode 450 may move laterally in a plane defined by the surface of the adhesive film layer 430 by about 0.6 cm (about ¼ of an inch) while maintaining electrical contact with the conductive gel layer(s) 425.

The electrode patch 400 may further be provided with a backing 470 coupled to a surface (either on the subject side or the external side) of the adhesive film layer 430. The backing 470 may provide increased mechanical stability to the electrode patch 400 and/or facilitate handling of the electrode patch. The backing 470 may be formed from a material such as plastic and may be bonded to the adhesive film layer at one or more locations by, for example, welding, gluing, or other methods known in the art. In one embodiment, the backing 470 is removably attached to the external or upper surface (the surface opposite to that which is to be adhered to a subject's skin) of the adhesive film layer 430 and/or to any material disposed on the adhesive film layer. The backing 470 may be removed from the electrode patch 400 after the electrode patch 400 is secured to the skin of a subject. The portions of the electrical conductors 440 illustrated in FIG. 5 as extending over the backing 470 may be unsecured to the backing and sufficiently flexible to allow removal of the backing 470 from beneath. Alternatively, in some embodiments, the length of the electrical conductors 440 may be shortened so that the backing 470 may be removed without disturbing the electrical conductors. In some embodiments, the end portions of the electrical conductors 440 illustrated in FIG. 5 as extending over the backing 470 may be replaced with electrical contacts to which conductors, for example, wires, or a connector may be attached after the electrode patch 400 is secured to a subject.

Figure 6:
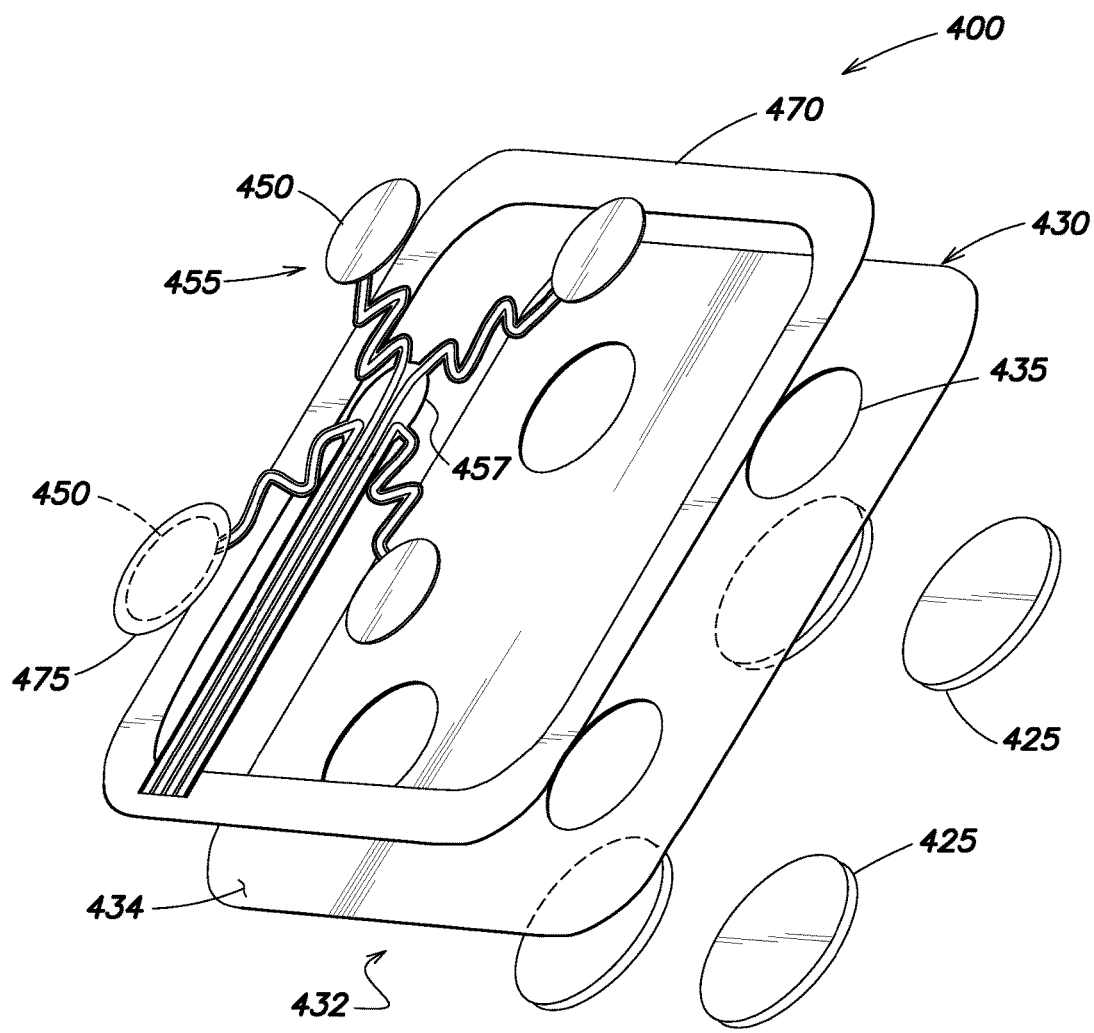
FIG. 6 is an exploded view of the multi-function electrode patch of FIG. 5.

FIG. 6 is an exploded view of the electrode patch 400 of FIG. 5 and illustrates the manner in which the electrode patch 400 may be formed in accordance with one embodiment of the present invention. An adhesive film layer 430 may be supplied with one or more apertures 435 formed therein. Conductive gel layers 425, illustrated in FIG. 6 as four disks, may be secured to a lower adhesive surface 432 of the adhesive film layer 430. The conductive gel layers may be formed with one or more lateral dimensions greater than one or more lateral dimensions (dimensions in the plane of the adhesive film layer) of the apertures 435. The conductive gel layers 425 may include portions which extend beyond the periphery of the apertures 435. These portions of the conductive gel layers 425 may adhere to the lower adhesive surface of the adhesive film layer 430. The lower adhesive surface 432 of the adhesive film layer 430 and the conductive gel layers 425 may be covered with a protective film (not shown) to prevent the adhesive layer from unintentionally adhering to objects prior to use. The protective film may be removed prior to applying the electrode patch 400 to a subject.

The patch 400 includes an electrode assembly 455 that is disposed above the adhesive film layer 430. The electrode assembly 455 includes a plurality of electrodes 450 and a corresponding plurality of electrical conductors 440 formed on a dielectric film 420. Each respective electrode 450 includes a conductive element 410 that defines a contact area 460 of the respective electrode. The conductive elements may be formed by depositing a conductive material on the dielectric film 420 (see FIG. 5). The electrical conductors 440 may be formed integrally with the conductive elements 410 on the dielectric film 420 or they may be formed separately and electrically connected to the conductive elements. The electrical conductors 440 may be covered with an insulating layer to electrically isolate them from an upper surface 434 of the adhesive film layer 430 and the subject's skin. The electrode assembly 455 may be placed on the upper surface 434 of the adhesive film layer 430 and positioned so that the contact area 460 of each respective electrode 450 is disposed above one or more of the apertures 435. The contact areas 460 may make electrical contact with the conductive gel layers 425 through the apertures 435. The conductive gel layers 425 help to maintain the electrode assembly 455 in a fixed position above the adhesive film layer 430.

The electrode assembly 455 may be secured directly to the upper surface 434 of the adhesive film layer 430 by, for example, an adhesive. Alternatively or additionally, one or more pieces of a second adhesive film 475 may be placed over one or more portions of the electrode assembly 455 to secure the one or more portions of the electrode assembly 455 between the one or more pieces of second adhesive film and the upper surface 434 of the adhesive film layer 430. As an example, for electrodes 450 having generally circular contact areas 460 as illustrated in FIGS. 5 and 6, circular portions of a second adhesive film 475 having radii greater than the contact areas 460 and/or the apertures 435 may be placed above the contact areas and adhered to the upper surface 434 of the adhesive film layer 430 at areas around the contact areas. An additional portion of the second adhesive film 475 (not shown) may secure a central portion 457 of the electrode assembly to the upper surface 434 of the adhesive film layer 430. Separately securing portions of the electrode assembly 455 to the adhesive film layer 430 may provide for these portions of the electrode assembly 455 to move relative to one another as skin of a subject to which the electrode patch 400 is secured moves or deforms. In other embodiments the second adhesive film may cover a greater portion, substantially all, or all of the portion of the electrode assembly disposed on the upper surface 434 of the adhesive film layer 430. The second adhesive film layer may be an insulating film, for example, a polyester film such as Mylar® polyester film or a film which facilitates that passage of water vapor, for example, Tegaderm™ wound care dressing film.

A backing 470, which may have a stiffness greater than the adhesive film layer 430 may be secured to the upper surface 434 of the adhesive film layer 430 and/or the second adhesive film and/or the electrode assembly 455. The backing 470 may be secured to one or more of these portions of the electrode patch 400 with a releasable adhesive, by the effect of static attraction to the electrode patch, or by other mechanisms known in the art. The backing 470 may provide mechanical stiffness to the electrode patch 400 to facilitate handling and/or transport, and may be removed once the electrode patch 400 is secured to a subject.

In the embodiments of the electrode patch 400 described with reference to FIGS. 5 and 6, the electrode patch 400 includes four electrode contact areas 460 in electrical contact with four conductive gel layers 425. Other embodiments of the electrode patch 400 may include greater or fewer than four electrode contact areas 460 or four conductive gel layers 425. For example, in some embodiments, the electrode patch 400 may include a single conductive gel layer 425 to which multiple electrode contact areas 460 may make electrical contact. The electrode patch 400 may include a multiple distinct conductive gel layers 425, with multiple electrode contact areas 460 making electrical contact with at least one of the distinct conductive gel layers 425. Other embodiments may include two distinct electrode contact areas 460 and conductive gel layers 425. Further embodiments may include a greater number, for example, five, six, seven, or more distinct electrode contact areas 460 and conductive gel layers 425. In addition, the conductivity of one or more of the gel layers may differ from the conductivity of others, depending on the desired functionality (e.g., defibrillation, pacing, ECG monitoring, etc.) of the corresponding electrodes.

It should be appreciated that a multi-electrode patch, such as that described above with respect to FIGS. 4, 5, and 6 can provide a number of benefits relative to electrode patches including only a single electrode. For example, as described above with respect to pacing, each electrode of the multi-electrode patch may be operated independently of the others to provide a portion of the pacing pulse to the subject. By spreading the pacing pulse over multiple electrodes, discomfort associated with the pacing pulse can be reduced, along with any associated trauma to the subject's skin. When used for monitoring an ECG of the subject, the presence of multiple electrodes permits different ECG vectors to be analyzed by examining signals provided by each of the different pairings of electrodes in the electrode patch, or between different pairings of electrodes in different electrode patches.

Where more than one, or all, of the individual electrodes are electrically coupled together or provided with the same signal, they may have an affect on the subject that is similar to a single electrode that is physically larger than any of the individual electrodes. For example, when disposed in close proximity with one another in the manner shown in FIG. 5 and provided with a defibrillation pulse, the affect on the subject is similar to that of a single circularly shaped electrode having a perimeter circumscribing the four individual electrodes, but with more flexibility, and with less surface area than the single electrode. Because the four electrodes have a smaller combined surface area than the equivalent single circularly shaped electrode, a lesser amount of the subject's skin is covered by the electrodes and associated gel layers below, thereby reducing the area of the subject's skin that may become irritated when the patch 400 is worn for prolonged periods of time. Pacing and/or defibrillation charges may be applied through one or more of the electrodes 450 at the same time as monitoring of the subject is being performed using one or more other of the electrodes 450.

The table in FIG. 7 illustrates a comparison between electrode dimensions for various electrode configurations. As can be seen from this table, an electrode system including a pair of round DF80 compliant electrode patches, each with an area of 75 cm$^2$ and placed at a subject's apex and sternum has a total electrode area of 150 cm$^2$ (75 cm$^2$ each) and a total electrode circumference of 30.69 cm for each electrode patch. Changing to a 75 cm$^2$ area square electrode for each of electrode patch again provides a total electrode area of 150 cm$^2$, but increases the total circumference to 34.64 cm for each patch. For an electrode system that includes a pair of electrode patches, each patch including four electrode segments and having half the total electrode surface area (75 cm$^2$) of either of the single electrode patch systems, the total electrode circumference for each electrode patch is increased to 43.41 cm. Reducing the size of the electrodes in the four electrode segment patch to have a combined circumference that is equal to that of the electrode in the single square electrode patch system results in a system with a total electrode area of only 47.77 cm$^2$. Reducing the size of the electrodes in the four electrode segment patch to have a combined circumference which is equal to that of the electrodes in the single round electrode patch results in a system with a total electrode area of only 37.5 cm$^2$. In tests performed with a pair of electrode patches, each having four round electrode segments having a radius of 1.22 cm (for a total area of 37.50 cm$^2$), it was found that this electrode system performed similarly to an electrode system including a pair of DF80 compliant round electrodes each with a radius of 4.89 cm (for a total area of 150.00 cm$^2$). Thus, by using electrode patches with four electrode segments rather than a single electrode, the electrode area may be reduced by 75% (37.5 cm$^2$ vs. 150 cm$^2$) while maintaining a same total electrode circumference (30.69 cm.) Without being bound to any particular theory, it is believed that conduction of electricity from an electrode into the skin of a subject may occur primarily at the periphery of an electrode. Thus, a system having a number of smaller electrodes with a given total circumference may perform in an electrically similar manner as a system having a single larger electrode of the same total circumference. The total area of the skin of a subject that is occluded by the electrodes may thus be reduced by using an electrode system with patches having multiple electrodes instead of patches with single electrodes. This, in turn, can result in a reduction in skin irritation and an increase in comfort for the subject.

The present invention is not limited to the shapes and relative sizes of the conductive gel layers 425, contact areas 460, and apertures 435 illustrated in FIGS. 5 and 6. One or more of these elements of the electrode patch 400 may be shaped differently, for example, as rectangles, triangles, squares, or any other polygon or curvaceous shape. In some embodiments one or both of the conductive gel layers 425 and the contact areas 460 may have a greater or smaller surface areas than the apertures 435. In some embodiments, one or more of the conductive gel layers 425, contact areas 460, and apertures 435 may be sized and/or shaped differently than one or more other of the conductive gel layers 425, contact areas 460, and apertures 435. Further, the electrode patch 400 as a whole may be formed in shapes other than a rectangle or rounded square as illustrated.

In some embodiments, portions of the electrode patch may be designed to facilitate the passage of water vapor, for example, evaporated sweat. For example, the adhesive film layer 430 and/or any film layers covering the electrode 450 may be formed of a material which provides for the passage of water vapor. This material may be, for example, Tegaderm™ wound care dressing film. The conductive gel layer(s) 425 may be formed from a hydrogel or other material as described below which provides for the passage of water vapor. In other embodiments, one or more portions of embodiments of the electrode patch 400 including, for example, portions of the adhesive film layer 430, portions of the electrode 450, portions of a dielectric film insulating an inner surface of the electrode 450 from the adhesive film layer 430, and/or portions of any film layers covering an outer surface of the electrode 450 may be perforated to facilitate the passage of water vapor from the skin of a subject to which the electrode patch is adhered.

In accordance with another aspect of the present invention, an electrode patch or system as described in any of the embodiments above may be utilized in conjunction with a conductive body paint. The conductive body paint may be applied to the skin of a subject prior to application of the electrode system, with or without a conductive gel layer therebetween. The electrode system would be positioned such that at least one electrode (or electrode segment) and any associated conductive gel layer contacted a portion of the skin of the subject to which the conductive paint had been applied. This would have the effect of lowering the impedance of the system and may provide for the utilization of even smaller areas of conductive gel. Furthermore, the conductive paint may create a barrier between the skin and the conductive gel, which may increase the wearability of the electrode system. For example, in empirical testing, a conductive paint such as Bare Paint™, available from Bare Conductive, Ltd. was applied to the body of a subject and found to reduce the impedance between a conductive surface of an electrode and the subject's skin by approximately 20%-30% relative to the same electrode without the conductive paint. Other types of conductive paint, having a demonstrated lack of toxicity may be used with electrodes, electrode patches, and electrode systems in accordance with the present invention, as well as with conventional electrodes and electrode systems.

The conductive gel layer included in electrodes in accordance with various embodiments disclosed herein may include a conductive polymer hydrogel, gel pad, gel sponge, or conductive fluid. The conductive gel layer may be adhesive to skin. The conductive gel layer may comprise a material that may be applied to the skin of a subject for extended-wear time periods of greater than, for example, about a week and up to about two weeks without causing significant skin irritation in areas where conductive gel layer contacts the skin of the subject. The conductive gel layer may be less irritating to the skin of a patient than conventional conductive hydrogels, for example, FW340 hydrogel, available from First Water Limited, Promeon RD-63B hydrogel, available from Tyco Healthcare Group (d/b/a/ Covidien), or the hydrogels disclosed in U.S. Pat. No. 5,11,548 to Riazzi et al, issued Apr. 30, 1996, U.S. Pat. No. 5,800,685 to Perrault, issued Sep. 1, 1998, or U.S. Pat. No. 7,076,282 to Munroe et al., issued Jul. 11, 2006. Suitable hydrogels of which the conductive gel layer may be comprised include FW266 hydrogel (First Water Limited), FW350 hydrogel (First Water Limited), FW340 BD hydrogel (First Water Limited), or one or more of the bioadhesive compounds disclosed in U.S. Pat. No. 6,447,798 to Munro et al., issued Sep. 10, 2002, which is hereby incorporated herein by reference in its entirety.

In some embodiments, the conductive gel comprises an aqueous plasticizer, a copolymer of a hydrophilic unsaturated water-soluble first monomer and a hydrophilic unsaturated water-soluble second monomer, and a cross-linking agent.

The conductive gel is may be obtained by polymerizing an aqueous reactive mixture comprising the first monomer, the second monomer, and a crosslinking agent.

In some embodiments, the first and second monomers are acrylate based monomers selected for their ability to polymerize rapidly in water and having substantially the same molecular weight whereby in a mixture of the two the relative proportions may be varied without significantly altering the molar characteristics of the composition.

In some embodiments, the first monomer is a compound having the formula

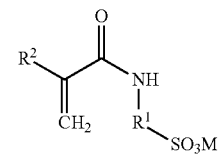

wherein in some embodiments $R^1$ represents a hydrocarbon moiety, $R^2$ represents hydrogen, a methyl group, or an ethyl group, and M represents hydrogen or a cation.

In some embodiments $R^1$ is an alkyl, cycloalkyl, or aromatic moiety. $R^1$ may represent a saturated moiety or an aromatic moiety. $R^1$ may contain from 3 to 12 carbon atoms, and in some embodiments, from 3 to 6 carbon atoms. In some embodiments $R^1$ represents a moiety having the formula

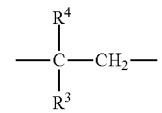

wherein $R^3$ represents hydrogen or a straight or branched chain alkyl group possessing from 1 to 6 carbon atoms and $R^4$ represents a straight or branched chain alkyl group possessing from 1 to 6 carbon atoms.

In some embodiments the second monomer is a compound having the formula

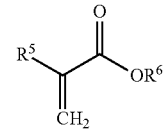

wherein $R^5$ represents hydrogen, a methyl group, or an ethyl group, $R^6$ represents hydrogen, a cation, or $R^7SO_3$ wherein $R^7$ represents an alkylene moiety of 1 to 4 carbon atoms. In some embodiments $R^7$ represents n-propyl.

Any one or more of $R^1$, $R^2$, $R^3$, $R^4$, $R^5$, and $R^7$ may be substituted by a group which has a tendency to increase the water solubility of the compound. Suitable groups will be well known to a person of skill in the art. Examples of optional substituents include a hydroxyl, amino, or ammonium group, or a halogen (for example chlorine, bromine, or iodine) atom. A suitable cation is an alkali metal cation, for example, sodium or potassium.

In some embodiments the first monomer is 2-acrylamido-2-methylpropanesulphonic acid, an analogue thereof, or one of its salts, for example, an alkali metal salt such as a sodium, potassium, or lithium salt. The second monomer is in some embodiments an acrylic acid, an analogue thereof, or one of its salts, for example, an alkali metal salt of one of sodium, potassium, or lithium. In other embodiments, the second monomer is a polymerizable sulphonate or a salt, for example, an alkali metal salt of one of sodium, potassium, or lithium, or of acrylic acid (3-sulphopropyl)ester or an analogue thereof. Examples of these respective monomers include the sodium salt of 2-acrylamido-2-methylpropanesulphonic acid, commonly known as NaAMPS, and acrylic acid (3-sulphopropyl)ester potassium salt, commonly known as SPA. NaAMPS is available commercially at present from The Lubrizol Corporation as either a 50% aqueous solution (reference code LZ2405) or a 58% aqueous solution (reference code LZ2405A). SPA is available commercially in the form of a solid from Raschig GmbH.

The total monomer content in the aqueous reactive mixture is in some embodiments from about 15% by weight to about 60% by weight, and in some embodiments from about 20% by weight to about 50% by weight.

Where the first monomer is a salt of AMPS and the second monomer is a salt of acrylic acid, the ratio by weight of the first monomer to the second monomer is in some embodiments not less than about 2:1 and in some embodiments not less than about 3:1. Where the first monomer is a salt of AMPS and the second monomer is a salt of acrylic acid (3-sulphopropyl)ester, the ratio by weight of the first monomer to the second monomer is in some embodiments not less than about 1:10, and in some embodiments not less than about 1:1.

In some embodiments the first monomer is included in an amount by weight of from about 1% to about 60%, in some embodiments from about 5% to about 50%, and in some embodiments from about 15% to about 40%. In some embodiments the second monomer is included in an amount by weight of from about 1% to about 50%, in some embodiments from about 10% to about 30%, and in some embodiments from about 10% to about 20%. In some embodiments the crosslinker is included in an amount of from about 0.01% by weight to about 2% by weight, and in some embodiments from about 0.1% by weight to about 2% by weight. The balance of the composition may comprise an aqueous plasticizer.

One advantage of the first and second monomers described above is that it has been found that high monomer content solutions can be achieved (approximately 75%). It has also been found that the second monomer is in some embodiments soluble in polyhydric alcohols such as glycerol. In some embodiments addition of glycerol to the first and second monomer mixture enhances the solubilization process. It has been found that the combination of the two monomers enables a greater control over water content than can be achieved otherwise. This can be important because it has also been found that compositions made with the final water content as an integral part of the pre-gel mix have different properties from those made with an excess of water and then dried to the final composition. For example, hydrogels with a final composition obtained by the evaporation of water generally have lower elastic or storage moduli than those made with no evaporation of water. To obtain similar levels of elastic moduli, the amount of crosslinker required in the former materials is higher. The evaporation of water and extra crosslinker add to the cost of the process. This problem is avoided by some embodiments of the present invention where a final drying step is generally not required.

In some embodiments, conventional crosslinking agents are used to provide the necessary mechanical stability and to control the adhesive properties of the conductive gel. Examples of suitable crosslinkers include tripropylene glycol diacrylate, ethylene glycol dimethacrylate, alkoxylated triacrylate, polyethylene glycol diacrylate (PEG400 or PEG600), and methylene bis acrylamide.

The aqueous reactive mixture optionally further comprises a surfactant, an additional monomer, an electrolyte, a processing aid (which may include a hydrophobic polymer), a water soluble polymer suitable for forming an interpenetrating polymer network, a non-hydrophilic polymer, and/or an antimicrobial agent (for example, citric acid or stannous chloride).

Embodiments of the process used to prepare the conductive gel may comprise mixing the ingredients to provide a reaction mixture in the form of an initial pre-gel aqueous based liquid formulation, which is then converted into a gel by a free radical polymerization reaction. This may be achieved by, for example, using conventional thermal initiators and/or photoinitiators or by ionizing radiation. Photoinitiation is a method used in some embodiments. Photoinitiation may be applied by subjecting the pre-gel reaction mixture containing an appropriate photoinitiation agent to UV light after it has been spread or coated as a layer on siliconized release paper or on another suitable solid substrate. The processing may be carried out in a controlled manner involving a precise predetermined sequence of mixing and thermal treatment or history. One feature of the process according to some embodiments of the invention is that no water is removed from the conductive gel (or hydrogel) after manufacture.

The conductive gel according to some embodiments of the invention comprises one or more additional monomers. A suitable additional monomer is an ionic monomer, for example, a cationic monomer. Additional monomers, when present, may be included in an amount of up to about 10% by weight.

An example of a suitable cationic monomer is a quaternary ammonium salt. Particular examples of suitable cationic monomer include (3-acrylamidopropyl)trimethyl ammonium chloride or [2-(acryloyloxy)ethyl]trimethyl ammonium chloride.

Some embodiments of conductive gels according to the invention comprise, in addition to a crosslinked polymeric network, an aqueous plasticizing medium. Plasticizers may be used to control adhesive properties of the conductive gels.

In some embodiments, the aqueous plasticizing medium additionally comprises a polymeric or non-polymeric polyhydric alcohol (such as glycerol), an ester derived therefrom, and/or a polymeric alcohol, for example, polyethylene oxide. Glycerol is one example of a suitable plasticizer. An alternative plasticizer is an ester derived from boric acid and a polyhydric alcohol such as glycerol. In some embodiments the aqueous reactive mixture comprises from about 10% by weight to about 50% by weight, and in some embodiments from about 10% by weight to about 45% by weight, of a plasticizer other than water.

Some embodiments of the conductive gel additionally comprise a water soluble polymer suitable for forming an interpenetrating polymer network. Hydrogels based on interpenetrating polymer networks (IPN) are well known. An IPN has been defined as a combination of two polymers, each in network form, at least one of which has been synthesized and/or crosslinked in the presence of the other. As will be appreciated, this combination will generally be a physical combination rather than a chemical combination of the two polymers. IPN systems may be described by way of example as follows:

Monomer 1 is polymerized and crosslinked to give a polymer which is then swollen with monomer 2 plus its own crosslinker and initiator.

If only one polymer in the system is crosslinked, the network formed is called a semi-IPN. Although they are also known as IPNs, it is only if there is total mutual solubility that full interpenetration occurs. In most IPNs there is, therefore, some phase separation but this may be reduced by chain entanglement between the polymers. It has also been reported that semi-IPNs can be made in the presence of carrier solvents, for example, water in the case of hydrophilic components.

It has been found that polymerizing and crosslinking water soluble monomers in the presence of water soluble polymers, water, and polyhydric alcohols produces hydrogel materials with enhanced rheological and consequently adhesive properties.

Suitable water soluble polymers for the formation of semi-IPNs include poly(2-acrylamido-2-methylpropanesulphonic acid) or one of its salts and its copolymers, poly (acrylic acid-(3-sulphopropyl) ester potassium salt), copolymers of NaAMPS and SPA, polyacrylic acid, polymethacrylic acid, polyethylene oxide, polyvinyl methyl ether, polyvinyl alcohol, polyvinylpyrrolidone, its copolymers with vinyl acetate, dimethylaminoethyl methacrylate, terpolymers with dimethylaminoethyl methacrylate and vinylcaprolactam, polysaccharides such as gum arabic, karaya gum, xanthan gum, guar gum, carboxymethyl cellulose (CMC), NaCMC, hydroxypropylmethyl cellulose (HPMC), hydroxyethyl cellulose (HEC) or combinations thereof.

The amount of interpenetrant polymer used will be dependent on the mechanical and rheological properties required as well on consideration of processing conditions. If the interpenetrant polymer used increases the viscosity of the pre-gel mix beyond 5,000 centipoise it has been found that the monomers do not polymerize and crosslink on an acceptable time scale (an acceptable time scale being, for example, less than 60 seconds or less than 10 seconds). The viscosity of the pre-gel mix depends on the nature and molecular weight of the interpenetrant and the nature of pre-gel processing.

Of the natural polysaccharides, gum arabic or maltodextrin is utilized in some embodiments due to its cold water solubility and lesser effect on viscosity compared with, for example, karaya gum. A higher concentration of gum arabic than karaya may therefore be used if desired, enabling a wider control of hydrogel properties. It has also been found that the processing steps for assembling the pre-gel formulation can influence the properties of the manufactured hydrogel. For a given formulation, if the components are assembled at 25° C. and cured different adhesive properties are obtained compared to those that have been heated to 70° C. Solutions containing natural polysaccharides become less opaque, indicative of improved solubility. The activity of water in compositions prepared from heat treated pre-gels generally is lower than in non heat treated pre-gels.

Conductive gels in accordance with some embodiments of the present invention comprise a hydrophobic polymer. Hydrophobic polymers may be incorporated either in the presence or absence of interpenetrant polymers to form phase separated materials. The preparation of two phase composites consisting of a hydrophilic polymer containing an ionically conducting continuous phase and domains of a hydrophobic pressure sensitive adhesive which enhance adhesion to mammalian skin have been reported in U.S. Pat. No. 5,338,490 to Dietz et al., issued Aug. 16, 1994, which is hereby incorporated herein by reference in its entirety. The method of preparation described therein involves casting a mixture (as a solution and or suspension) consisting of the hydrophilic polymer containing phase and hydrophobic components onto a substrate and then removing the solvent. It has been found, however, that adhesive ionically conducting hydrogels may be better prepared by combining the hydrophobic polymer (for example, as an emulsion) with the components of the pre-gel reaction mixture and casting these onto a substrate and curing. In some embodiments, there is no need to remove a solvent in order to form useful materials. Furthermore, the hydrophilic phase of the composition, in addition to being a crosslinked network, may also be an IPN or semi-IPN.

Embodiments of a conductive gel in accordance with the present invention may include a hydrophobic pressure sensitive adhesive selected from the group consisting of polyacrylates, polyolefins, silicone adhesives, natural or synthetically derived rubber base and polyvinyl ethers or blends thereof. The hydrophobic pressure sensitive adhesive in these embodiments may be an ethylene/vinyl acetate copolymer such as that designated DM137 available from Harlow Chemical Company Ltd. or vinyl acetate dioctyl maleate such as that designated Flexbond 150 and sold by Air Products and Chemicals, Inc. Those skilled in the art will also know that the molecular weight and comonomer ratios may be altered to control the properties of hydrophobic pressure sensitive adhesives. In general, the degree of surface segregation exhibited by such hydrophobic pressure sensitive adhesive (HPSA) will be dependent on factors such as composition of the HPSA, viscosity of the pre-gel mixture, temperature and rate of curing.

It is believed that when hydrophobic polymers are incorporated in this way that the hydrophobic component segregates to the surface (as determined by Fourier transform infrared attenuated total reflectance spectroscopy, FTIR ATR, approximate sampling depth 1 μm using a ZnSe crystal or 0.25 μm with a germanium crystal) and that it is the amount of the hydrophobic component present in the surface that influences the adhesion to a wide variety of materials. The greater the amount of the hydrophobic component in the surface, the greater the adhesion of the conductive gel to skin. In U.S. Pat. No. 5,338,490 weight ratios of the hydrophilic phase to the hydrophobic phase of 60:1 to 8:1 were claimed. In conductive hydrogels of between about 100 μm and about 2,000 μm thick made in accordance with embodiments of the present invention, the ratio of hydrophilic to hydrophobic components may range from about 7:1 to about 1:20. In embodiments of processes in accordance with the present invention it may take up to 72 hours from the initial curing of the conductive hydrogel for the segregation of the hydrophobic materials to the surface, as defined by the ATR sampling depth, to be complete.

Conductive gels in accordance with some embodiments of the present invention include a relative amount of hydrophobic polymer (which is the amount of hydrophobic polymer relative to the amount of monomer) which is at least about four times greater, and in some embodiments, at least about eight times greater, at the surface of the conductive gel layer compared to what it is in the bulk of the conductive gel.

Here, the surface may be considered extending to a depth of between about 0.25 μm to about 1 μm into the bulk of the conductive gel layer. The relative amount of hydrophobic polymer may be measured by obtaining the ratio of the peak height of the peak in the carbonyl region for the hydrophobic polymer to the peak height of the peak in the carbonyl region for the first monomer, using the relevant FTIR ATR technique. The wave number values for the relevant peaks for the hydrophobic polymer and the monomer are well known.

Conductive gels in accordance with the present invention optionally include a surfactant. Any compatible surfactant may be used. Nonionic, anionic and cationic surfactants may be used, either alone or in combination. In some embodiments the surfactant is included in an amount from about 0.1% by weight to about 20% by weight, and in some embodiments from about 0.1% by weight to about 10% by weight.

Having now described some illustrative embodiments, it is apparent that the foregoing is illustrative and not limiting, having been presented by way of example. In particular, although many of the examples presented herein involve specific combinations of method acts or system elements, those acts and those elements may be combined in other ways. Acts, elements and features discussed only in connection with one embodiment are not intended to be excluded from a similar role in other embodiments.

Note that in FIGS. 1 through 6, the enumerated items are shown as individual elements. In actual implementations of the systems and methods described herein, however, they may be part of or inseparable components of other elements.

EXAMPLE

An electrode as described above including a conductive gel layer comprising FW340 hydrogel (First Water Limited) was electrically tested in accordance with the ANSI/AAMI DF80:2003 medical electrical equipment standard for the safety of cardiac defibrillators. The results of this testing are shown in Table 1 below:

The results of these tests indicate that the electrode including the FW340 hydrogel as a conductive gel layer passed all of the electrical safety tests of ANSI/AAMI DF80:2003 to which it was subjected.

Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements to single or plural configurations. References to any act or element being based on any information, act or element may include embodiments where the act or element is based at least in part on any information, act, or element.

Any embodiment disclosed herein may be combined with any other embodiment, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. Such terms as used herein are not necessarily all referring to the same embodiment. Any embodiment may be combined with any other embodiment, inclusively or exclusively, in any manner consistent with the aspects and embodiments disclosed herein.

References to "or" may be construed as inclusive so that any terms described using "or" may indicate any of a single, more than one, and all of the described terms. Embodiments, acts, or elements are not essential unless recited as such.

One skilled in the art will realize the systems and methods described herein may be embodied in other specific forms without departing from the characteristics thereof. For example, electrode components may have shapes other than circular and rectangular. Electrode components can be circular, elliptical, quadrilateral, square, or other designs, and can have different sizes for larger (for example adult or

TABLE 1

Electrode Performance at 360 Joules Tested per ANSI/AAMI DF80: 2003

| DF80 Test | | | Test Results ECG Moniotring, Defib/Cardioversion, Pacing | |
|---|---|---|---|---|
| Number | Test Name | Specification | Without Pacing | Defib After 8-Hr Pacing |
| 105.3 (also EN 60601-2-4 105.3) | Recovery of ECG after Defibrilation | Loss of amplitude <50%, 10 sec. after 10 defibs | loss of amplitude <50% | not applicable |
| 57.10dd (also EN 60601-2-4 57.1-d) | Dielectric strength | >500 Mohms equates to <15 uA at 7,500 V | >500 Mohms, <1 uA | not applicable |
| 107.1.1 | AC small signal impedance at 10 Hz | <3000 Ohms | 167 Ohms | 3 Ohms |
| 107.1.1 | AC small signal impedance at 30 KHz | <5 Ohms | 1.3 Ohms | 1.5 Ohms |
| 107.1.2 | AC large signal impedance at Emax | <3 ohms | 1.0 Ohm | 1.1 Ohms |
| 107.1.3 | Combined offset instability & noise | <100 uV | 1 uV | 1 uV |
| 107.1.4 | Defibrilation overload recovery | <750 mV (<ECG aplifier cut-off) | 527 mV @ 4 sec 416 mV @ 60 sec | 679 mV @ 4 sec 667 mV @ 60 sec |
| 107.1.5 | DC offset voltage | <750 mV (<ECG aplifier cut-off) | 9 mV | 687 mV | obese) or smaller (child, pediatric, or neonatal) subjects. Electrodes configured for placement on a particular part of the subject's anatomy (for example, chest, back, legs, head) can be ergonomically configured to adhere to that anatomical feature. A plurality of electrodes can be placed on one region of the subject, for example, two electrodes can be placed on the subject's chest, back, or lateral portion, with at least one other electrode placed at another location on the subject. Electrodes can be concave or convex. Electrodes can have more fanciful or arbitrary shapes or patterns (e.g., star, unicorn, smiley face, dinosaur, football, baseball, soccer ball, basketball, celebrity, athletic, or cartoon) to, for example, ease the mental anguish of a child with a medical condition who wears the electrode. Further, electrode components depicted in phantom are part of the electrode and merely may not be entirely visible from the perspective of the associated drawings. Electrodes in accordance with the present invention may communicate with other circuitry via conducting wires or wirelessly.

The foregoing embodiments are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An electrode comprising:
   a conductive element; and
   a hydrogel covering at least a portion of a surface of the conductive element, the conductive element and the hydrogel having a combined AC large signal impedance of about 1 Ohm to about 3 Ohms as tested in accordance with the method of the ANSI/AAMI DF80:2003 medical electrical equipment standard for the safety of cardiac defibrillators, the hydrogel not resulting in significant skin irritation on a human subject as tested in accordance with the method of ANSI/AAMI/ISO standard 10993-1 after a period of at least about one week,
   the electrode being disposed in an electrode patch, the electrode patch comprising an adhesive film layer configured to substantially surround the conductive element and adhere to skin of the subject, the electrode being laterally movable in a plane of the electrode patch and relative to one or more other electrodes disposed in the electrode patch.

2. The electrode of claim 1, wherein the electrode provides similar electrical performance during defibrillation as an electrode compliant with the ANSI/AAMI DF80:2003 medical electrical equipment standard for the safety of cardiac defibrillators.

3. The electrode of claim 2, wherein the hydrogel comprises an aqueous plasticizer, a copolymer of a hydrophilic unsaturated water-soluble first monomer, a hydrophilic unsaturated water-soluble second monomer, and a cross-linking agent.

4. The electrode of claim 3, wherein the first monomer is a compound of the formula

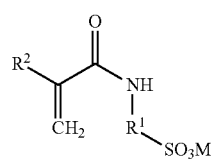

wherein $R^1$ is selected from the group consisting of a hydrocarbon moiety, a hydroxyl group, an amino group, an ammonium group, a halogen, and an alkali metal cation, $R^2$ is selected from the group consisting of hydrogen, a methyl group, an ethyl group, a hydroxyl group, an amino group, an ammonium group, a halogen, and an alkali metal cation, and M is selected from the group consisting of hydrogen and a cation.

5. The electrode of claim 4, wherein $R^1$ is selected from the group consisting of alkyl, cycloalkyl, and an aromatic moiety containing from 3 to 12 carbon atoms.

6. The electrode of claim 4, wherein $R^1$ represents

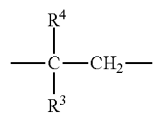

wherein $R^3$ is selected from the group consisting of hydrogen, an alkyl group possessing from 1 to 6 carbon atoms, a hydroxyl group, an amino group, an ammonium group, a halogen, and an alkali metal cation, and $R^4$ is selected from the group consisting of an alkyl group possessing from 1 to 6 carbon atoms, a hydroxyl group, an amino group, an ammonium group, a halogen, and an alkali metal cation.

7. The electrode of claim 6, wherein the second monomer is a compound of the formula

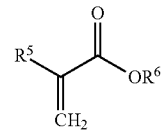

wherein $R^5$ is selected from the group consisting of hydrogen, a methyl group, an ethyl group, a hydroxyl group, an amino group, an ammonium group, a halogen, and an alkali metal cation, and $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

8. The electrode of claim 4, wherein the second monomer is a compound of the formula

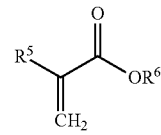

wherein $R^5$ is selected from the group consisting of hydrogen, a methyl group, an ethyl group, a hydroxyl group, an amino group, an ammonium group, a halogen, and an alkali metal cation, and $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

9. The electrode of claim 1, wherein the electrode is coupled to an electrical conductor that allows the electrode to move relative to the electrode patch.

10. The electrode of claim 9, wherein the electrical conductor is formed with a zig-zag shape.

11. The electrode of claim 1, wherein each of the electrodes disposed in the electrode patch are laterally movable in the plane of the electrode patch relative to each other of the electrodes disposed in the electrode patch.

12. An electrode patch comprising:
an adhesive film layer having a first surface and a second surface opposite the first surface, the second surface configured to adhere to skin of a subject; and
a plurality of electrodes disposed in the electrode patch, at least one of the plurality of electrodes including a conductive element substantially surrounded by the adhesive film layer, and a hydrogel covering at least a portion of a surface of the conductive element, the conductive element contacting the hydrogel through an aperture in the adhesive film layer, the conductive element and the hydrogel having a combined AC large signal impedance of about 1 Ohm to about 3 Ohms as tested in accordance with the method of the ANSI/AAMI DF80: 2003 medical electrical equipment standard for the safety of cardiac defibrillators, the hydrogel not resulting in significant skin irritation on a human subject as tested in accordance with the method of ANSI/AAMI/ISO standard 10993-1 after a period of at least about one week, the at least one of the plurality of electrodes being laterally movable in a plane of the electrode patch and relative to one or more other of the plurality of electrodes disposed in the electrode patch.

13. The electrode patch of claim 12, wherein the electrode patch provides similar electrical performance during defibrillation as an electrode compliant with the ANSI/AAMI DF80:2003 medical electrical equipment standard for the safety of cardiac defibrillators.

14. The electrode patch of claim 13, wherein the hydrogel comprises an aqueous plasticizer, a copolymer of a hydrophilic unsaturated water-soluble first monomer, a hydrophilic unsaturated water-soluble second monomer, and a cross-linking agent.

15. The electrode patch of claim 14, wherein the first monomer is a compound of the formula

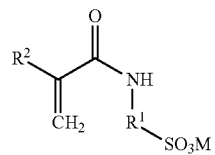

wherein $R^1$ is selected from the group consisting of a hydrocarbon moiety, a hydroxyl group, an amino group, an ammonium group, a halogen, and an alkali metal cation, $R^2$ is selected from the group consisting of hydrogen, a methyl group, an ethyl group, a hydroxyl group, an amino group, an ammonium group, a halogen, and an alkali metal cation, and M is selected from the group consisting of hydrogen and a cation.

16. The electrode patch of claim 15, wherein the second monomer is a compound of the formula

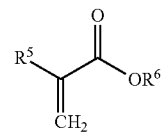

wherein $R^5$ is selected from the group consisting of hydrogen, a methyl group, an ethyl group, a hydroxyl group, an amino group, an ammonium group, a halogen, and an alkali metal cation, and $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

17. The electrode patch of claim 14, wherein a first of the plurality of electrodes and a second of the plurality of electrodes are spaced equidistant from a third of the plurality of electrodes.

18. The electrode patch of claim 14, wherein at least two of the plurality of electrodes share a common electrical connection.

19. The electrode patch of claim 14, wherein at least two of the plurality of electrodes can be selectively electrically coupled together.

20. The electrode patch of claim 12, wherein the aperture has one or more dimensions greater than one or more dimensions of the conductive element, a spacing being defined between an outer periphery of the conductive element and inner edges of the aperture.

21. The electrode patch of claim 12, wherein the aperture has one or more dimensions smaller than one or more dimensions of the hydrogel, portions of the hydrogel extending below the adhesive film layer beyond an area defined by the aperture.

22. A biomedical electrode system, comprising:
a first electrode disposed in an electrode patch and configured to adhere to a first location of a subject; and
a second electrode disposed in the electrode patch and configured to adhere to a second location of the subject;
the first electrode including:
an adhesive film layer having a first surface and a second surface opposite the first surface, the second surface configured to adhere to skin of the subject;
a conductive element substantially surrounded by the adhesive film layer; and
a hydrogel covering at least a portion of a surface of the conductive element, the conductive element contacting the hydrogel through an aperture in the adhesive film layer, the conductive element and the hydrogel having a combined AC large signal impedance of less than about 1 Ohm to about 3 Ohms as tested in accordance with the method of the ANSI/AAMI DF80: 2003 medical electrical equipment standard for the safety of cardiac defibrillators, the hydrogel not resulting in significant skin irritation on a human subject as tested in accordance with the method of ANSI/AAMI/ISO standard 10993-1 after a period of at least about one week, the first electrode being laterally movable in a plane of the electrode patch and relative to the second electrode.

23. The biomedical electrode system of claim 22, wherein the hydrogel does not result in significant skin irritation on a human subject as tested in accordance with the method of ANSI/AAMI/ISO standard 10993-1 after a period of at least about two weeks.

24. The biomedical electrode system of claim 22, wherein the hydrogel comprises an aqueous plasticizer, a copolymer of a hydrophilic unsaturated water-soluble first monomer, a hydrophilic unsaturated water-soluble second monomer, and a cross-linking agent.

25. The biomedical electrode system of claim 24, wherein the first monomer is a compound of the formula

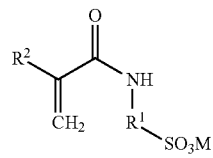

wherein $R^1$ is selected from the group consisting of a hydrocarbon moiety, a hydroxyl group, an amino group, an ammonium group, a halogen, and an alkali metal cation, $R^2$ is selected from the group consisting of hydrogen, a methyl group, an ethyl group, a hydroxyl group, an amino group, an ammonium group, a halogen, and an alkali metal cation, and M is selected from the group consisting of hydrogen and a cation.

26. The biomedical electrode system of claim 25, wherein the second monomer is a compound of the formula

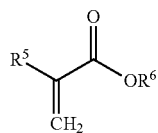

wherein $R^5$ is selected from the group consisting of hydrogen, a methyl group, an ethyl group, a hydroxyl group, an amino group, an ammonium group, a halogen, and an alkali metal cation, and $R^6$ is selected from the group consisting of hydrogen, a cation, and $R^7SO_3$, wherein $R^7$ is selected from the group consisting of an alkylene moiety of 1 to 4 carbon atoms, a hydroxyl group, an amino group, an ammonium group, a halogen, and an alkali metal cation.

27. An electrode comprising:

a conductive element; and a hydrogel covering at least a portion of a surface of the conductive element, the conductive element and the hydrogel having a combined AC large signal impedance of about 1 Ohm to about 3 Ohms as tested in accordance with the method of the ANSI/AAMI DF80:2003 medical electrical equipment standard for the safety of cardiac defibrillators, the hydrogel not resulting in significant skin irritation on a human subject as tested in accordance with the method of ANSI/AAMI/ISO standard 10993-1 after a period of at least about one week, the electrode being disposed in an electrode patch, the electrode patch comprising an adhesive film layer configured to substantially surround the conductive element and adhere to skin of the subject, the electrode having a moisture vapor transmission rate of between about 600 g/m²/day and about 1,400 g/m²/day at room temperature at a relative humidity of about 70%, the electrode being laterally movable in a plane of the electrode patch and relative to one or more other electrodes disposed in the electrode patch.

* * * * *